United States Patent [19]

Graham

[11] 4,440,748

[45] Apr. 3, 1984

[54] **STRAIN OF *ESCHERICHIA COLI* BY BACTERIAL CONJUGATION**

[75] Inventor: Amy C. Graham, Avenel, N.J.

[73] Assignee: Merck & Co., Inc., Rahway, N.J.

[21] Appl. No.: 373,388

[22] Filed: Apr. 3, 1982

[51] Int. Cl.$^3$ .................... A61K 39/108; C12N 15/00; C12N 1/20

[52] U.S. Cl. ........................................ 424/92; 424/88; 424/93; 435/172; 435/253

[58] Field of Search ............................ 424/92, 88, 93; 435/253, 172, 173

[56] References Cited

U.S. PATENT DOCUMENTS

| | | | |
|---|---|---|---|
| 3,975,517 | 8/1976 | Wilson | 424/92 |
| 4,237,115 | 12/1980 | Brinton, Jr. | 424/92 |
| 4,298,597 | 11/1981 | Acres et al. | 424/92 |
| 4,311,797 | 1/1982 | Khachotourians | 424/92 |
| 4,338,298 | 7/1982 | Myers | 424/92 |
| 4,343,792 | 8/1982 | Gouet et al. | 424/92 |

OTHER PUBLICATIONS

Metzler, D., Biochemistry, Academic Press, New York pp. 945–946, 1977.
Lamanna, C., et al., Basic Bacteriology, The Williams & Wilkins Company, Baltimore, pp. 722–727, 1965.
DeGraff et al., Infection and Immunity, 33, pp. 877–883 (1981).
Altmann et al., Biochemistry Journal, 201, pp. 505–513 (1982).
Korhonen et al., Infection and Immunity, 27, pp. 569–575 (1980).
Wilson et al., "Bacterial Genetics" from Life on Earth, pp. 223–226, Sinaver Assoc. Inc., Publishers Stamford, Ct. (1973).
Srb et al., "Recombination Mechanisms in Bacteria" from General Genetics Second Edition, pp. 173–176, W. H. Freeman & Co. Publishers, San Francisco, Ca. (1965).
Gaastra et al., Microbiological Reviews, 46, pp. 129–161 (1982).

*Primary Examiner*—Blondel Hazel
*Attorney, Agent, or Firm*—David L. Rose; William H. Nicholson; Mario A. Monaco

[57] ABSTRACT

A new strain of *Escherichia coli* which is enteropathogenic to both calves and piglets is produced by bacterial conjugation of two parents, one enteropathogenic solely to calves and one enteropathogenic solely to piglets. The new strain is useful in the preparation of a vaccine for use in both calves and piglets to prevent colibacillosis.

5 Claims, No Drawings

STRAIN OF *ESCHERICHIA COLI* BY BACTERIAL CONJUGATION

BACKGROUND OF THE INVENTION

This invention is concerned with a new strain of *Escherichia coli* which is enteropathogenic to both calves and piglets, and to a colibacillosis vaccine prepared therefrom.

Colibacillosis, commonly called (white) scours, is an enteric disease of which diarrhea is the major symptom and is caused by strains of *E. coli* pathogenic to a particular species of animal. The species specificity is determined by the type of pilus attachment factor elaborated by the infecting *E. coli*. Strains pathogenic to calves share a common pilus antigen, K99, while three different pilus antigens, K88, K99 and 987, are associated with pathogenicity in piglets. Thus a vaccine containing only K99 pili would be species specific for calves, while any vaccine containing only one type of pilus could not be fully protective in piglets. A vaccine that was not species specific would require a combination of cellular material from at least two organisms. Combination vaccines are known but they have several disadvantages such as large manufacturing volumes, large doses, and the questionable practice of introducing to the host non-efficacious bacterial antigens.

Now, with the present invention there is provided a new strain of *Escherichia coli* that is enteropathogenic to both calves and piglets and useful for preparation of a polyvalent bacterial colibacillosis vaccine to prevent colibacillosis caused by either K88+ or K99+ *E. coli*.

There is also provided by this invention a process for preparing the new strain of *E. coli* by bacterial conjugation.

There is further provided a monovalent colibacillosis vaccine prepared from one strain of *E. coli* for use in both calves and piglets and a method of prophylactic treatment of colibacillosis in calves and piglets, with the new vaccine.

DETAILED DESCRIPTION OF THE INVENTION

The novel microorganism of this invention is identified as MB 4518, is a strain of *Esherichia coli* carrying both K88 and K99 antigens and has been deposited with the American Type Culture Collection, 12301 Parklawn Drive, Rockville, Md., U.S.A., 20582, receiving accession number ATCC No. 39076.

The novel strain of *E. coli* of this invention (ATCC No. 39076) is the product of bacterial conjugation of two other strains of *E. coli*:

1. Donor *Escherichia coli*, ATCC No. 39075 (MB 3981).

P155 *Escherichia coli* K88+, sensitive to nalidixic acid, has genes responsible for K88 antigen production which has been shown to be co-resident with genes specifying raffinose fermentation (Raf+) on a plasmid.

2. Recipient *Escherichia coli*, ATCC No. 39074 (MB 3857).

B44nal$^R$ *Escherichia coli* K99+ which is resistant to nalidixic acid and contains several large molecular weight plasmids, which specify production of both a heat stable enterotoxin, and the K99 antigen.

The novel process of this invention is a bacterial conjugation of donor bacteria, *E. coli*, ATCC No. 39075 with recipient bacteria, *E. coli*, ATCC No. 39074. It comprises the steps of:

(a) incubating together, the donor *E. coli* (K88+) which is sensitive to nalidixic acid and is able to utilize raffinose, and the recipient *E. coli* (K99+) which is resistant to nalidixic acid and unable to utilize raffinose, at about 37° C. for 8 to about 24 hours, preferably about 16 hours or "overnight";

(b) inoculating a defined nutrient medium containing raffinose as the only carbon source and nalidixic acid with some of the cell suspension obtained in step (a) and incubating at about 37° C. for about 2 to about 5 days, preferably about 3 days;

(c) isolating the viable cells from the incubation which, by definition, are resistant to nalidixic acid and are able to utilize raffinose, thus being neither parent.

The novel vaccine of this invention can be prepared in either of two ways. K88 and K99 antigen are isolated from the strain, purified, and used in a pilus vaccine to stimulate the production of antibody to both attachment factors. Specific anti-pilus antibodies prevent *E. coli* attachment but are not bactericidal. Alternatively the entire organism is used in a vaccine, following its inactivation. This stimulates antibody to the entire cell, rather then just to the pili, and provides additional protection by stimulating bactericidal antibody production.

EXAMPLE 1

Conjugation of Donor *E. coli* ATCC No. 39075 and Recipient *E. coli*, ATCC NO. 39074

1. Parental stock cultures were streaked onto agar media to obtain isolated colonies and their putative genotypes were verified.

2. A single colony of each was inoculated into individual tubes containing 5 milliliters of brain heart infusion broth and incubated overnight in a 37° C. incubator.

3. On the following day, a fresh tube of 5 ml of brain heart infusion broth was inoculated with one drop (approximately 50 microliters) each of the donor (P155) and the recipient (B44nal$^R$). This tube (the mating mixture) was then incubated overnight at 37° C.

4. On the following day, the mating mixture was centrifuged to allow removal of the cells from the surrounding medium.

5. The cell pellet was resuspended in 5 ml of salt solution (O salts)$^a$, recentrifuged, and finally suspended in 5 ml O salts.

6. The cell suspension was diluted in tenfold steps to a final dilution of $10^{-7}$.

7. Aliquots (0.1 ml) of $10^{-5}$, $10^{-6}$, and $10^{-7}$ dilutions were plated on indicator media containing raffinose (Drigalski-raf) to allow differentiation of the parentals. These plates were incubated overnight at 37° C.

8. The cell suspension (0.1 ml) and dilutions (0.1 ml) of $10^{-1}$ through $10^{-5}$ were plated on minimal media containing raffinose as the sole carbon source, O salts, and nalidixic acid (O-raf+nal) to select for nalidixic acid resistant cells which had acquired the ability to ferment raffinose. These plates were incubated for 72 hours at 37° C.

9. Colonies arising on O-raf+nal were restreaked on O-raf+nal to insure purity and incubated for 48 hours at 37° C.

10. The plasmid content of the repurified colonies was determined by the examination of cell lysates via agarose gel electrophoresis; one strain, designated AG750, was shown to contain the original B44 plasmids and to have additionally acquired the K88+-Raf+ plasmid from P155.

(a) O salts per liter
 2.0 g KH$_2$PO$_4$
 7.0 g K$_2$HPO$_4$
 1.0 g (NH$_4$)$_2$PO$_4$
 0.1 g MqSO$_4$ H$_2$O
 distilled H$_2$O to 1 liter

EXAMPLE 2

Pathogenicity of *E. Coli* ATCC No. 39076 For Calves and Piglets

*E. coli*, ATCC No. 39076 was shown to be capable of inducing scours in both calves and piglets. The nalidixic acid resistant *E. coli* was isolated from the feces of the infected animals to determine the plasmid content of the strain being excreted.

A. Calves. Four calves were inoculated with ATCC 39076. On day one post-infection all demonstrated evidence of scours, and feces were plated on EMB-nal plates to determine cell count per gram of feces. Either 25 or 50 colonies were picked from EMB-nal plates and plated onto Drigalski-raffinose plates. All the colonies were Raf+. By day 2, the proportion of Raf+ cells in the population was between 14–28% in two of the remaining calves. A third calf shed mostly Raf+ isolates (95%); this calf eventually recovered. The fourth calf died and was necropsied and samples from the jejunum, ileum and colon showed 40%, 64% and 100% Raf+ isolates respectively. By day 3, the two scouring calves were shedding 100% Raf− *E. coli;* one died on day 4 and one on day 6. The recovered calf continued to shed predominantly Raf+ isolates for 6 days. Cleared lysates were prepared from 24 of the isolates and the Raf− isolates were all shown to have lost the K88+-Raf+ plasmid. Thus in calves it seems the K88+-Raf+ plasmid is not stable in strain ATCC 39076.

B. Piglets. Three litters of piglets were infected with ATCC 39076 and the excretion of Raf+ Nal$^R$ *E. coli* monitored throughout the course of infection and at necropsy (either at death or 8 days PI). Almost no loss of the Raf+ phenotype was observed throughout the experiment, although rare Raf− isolates did appear. In one litter, the isolates from three piglets were chosen for closer study by cleared lysate analysis. Piglet No. 6 died on day 2; all isolates from day one and necropsy had the same plasmid content as ATCC 39076. Piglet No. 1 survived until day 6; isolates from days one through 5 and the small intestine at necropsy showed the same plasmids as ATCC 39076, as did 5/6 isolates from day 6. The one aberrant isolate from day 6 showed loss of the K88+-Raf+ plasmid and acquisition of a smaller plasmid which may be the result of a deletion in the K88+-Raf+ plasmid. One isolate from the colon at necropsy had lost the smaller of the resident B44 plasmids. Piglet No. 10 survived through day 9. All of the isolates from days one through 6, 8 and 9 were the same as ATCC 39076. One isolate from day 7 showed an aberrant pattern involving one of the resultant B44 plasmids, but the K88+ Raf+ plasmid was unaffected.

What is claimed is:

1. A biologically pure culture of a microorganism which is a strain of *Escherichia coli* synthesizing both K88 and K99 antigens, with access number ATCC 39076.

2. The microorganism of claim 1 prepared by bacterial conjugation of a donor *E. coli* (K88+, Raf+), ATCC 39075 and a recipient *E. coli* (K99+, Nal$^R$), ATCC 39074.

3. The microorganism of claims 1 or 2 which is enteropathogenic to calves and piglets with the ability to cause colibacillosis in both species.

4. A vaccine for prevention of colibacillosis comprising K88 and K99 pili purified from a strain of *Escherichia coli* with access number ATCC 39076 or the whole inactivated cell and a pharmaceutically acceptable carrier.

5. A process for the production of a microorganism which is a strain of *Escherichia coli* with both K88 and K99 antigens, with access number ATCC 39076 which comprises bacterial conjugation of a donor *E. coli* (K88+, Nal$^s$, Raf+), ATCC 39075, and a recipient *E. coli* (K99+, Nal$^R$), ATCC 39074 which comprises the steps of:

(a) incubating together the donor and recipient *E. coli* at about 37° C. for 8–24 hours;

(b) inoculating a nutrient medium containing raffinose as the only carbon source and nalidixic acid with some of the cells from Step (a) and incubating at about 37° C. for 2 to 5 days; and (c) isolating viable cells from step (b).

* * * * *